United States Patent [19]
Brubaker

[11] Patent Number: 5,864,017
[45] Date of Patent: Jan. 26, 1999

[54] METHODS OF FORMING A PRE-CLOTTED CLOT SUPPORTER, METHODS OF STORING A PRE-CLOTTED CLOT SUPPORTER AND CLOTS ADHERED TO FLUID PERMEABLE MEMBRANES

[75] Inventor: Daniel B. Brubaker, Clovis, Calif.

[73] Assignee: Espress Tech, Inc., Clovis, Calif.

[21] Appl. No.: 775,365

[22] Filed: Jan. 3, 1997

Related U.S. Application Data

[60] Division of Ser. No. 431,276, Apr. 28, 1995, Pat. No. 5,612,187, which is a continuation-in-part of Ser. No. 216,189, Mar. 22, 1994, Pat. No. 5,432,084.

[51] Int. Cl.$^6$ .............................. A61K 35/14; C12Q 1/56
[52] U.S. Cl. ................. 530/380; 530/381; 530/382; 435/2; 435/13; 435/69.6; 435/287.9; 422/68.1; 422/73
[58] Field of Search ................... 530/380, 381, 530/382; 435/2, 13, 69, 61, 287.9; 422/68.1, 73

[56] References Cited

U.S. PATENT DOCUMENTS

| | | | |
|---|---|---|---|
| 2,674,889 | 4/1954 | Toof | 73/432 |
| 2,878,715 | 3/1959 | Rhees et al. | 88/14 |
| 3,552,395 | 1/1971 | Bidwell et al. | 128/276 |
| 3,618,395 | 11/1971 | Melliger | 73/432 |
| 3,802,272 | 4/1974 | Bischoff et al. | 73/432 |
| 3,809,613 | 5/1974 | Vieth et al. | 195/63 |
| 3,865,549 | 2/1975 | Riley | 23/230 R |
| 3,865,726 | 2/1975 | Chibata et al. | 210/152 |
| 3,918,908 | 11/1975 | Moyer et al. | 23/230 B |
| 4,016,044 | 4/1977 | Fresnel et al. | 195/115 |
| 4,062,652 | 12/1977 | Rolfo-Fontana | 23/253 |
| 4,099,412 | 7/1978 | Nehrbass | 73/209 |
| 4,247,298 | 1/1981 | Ripple | 23/230 R |
| 4,335,438 | 6/1982 | Smolen | 364/497 |
| 4,604,894 | 8/1986 | Kratzer et al. | 73/64.1 |
| 4,606,420 | 8/1986 | Silver | 177/160 |
| 4,663,127 | 5/1987 | Jackson et al. | 422/58 |
| 4,681,858 | 7/1987 | Chaudhari et al. | 436/165 |
| 4,754,657 | 7/1988 | Schneider | 73/866 |
| 4,855,821 | 8/1989 | Swon et al. | 358/101 |
| 4,856,909 | 8/1989 | Mehtra et al. | 366/208 |
| 4,861,725 | 8/1989 | Liau | 435/294 |
| 4,928,603 | 5/1990 | Rose et al. | 106/124 |
| 4,953,561 | 9/1990 | Guirguis | 128/771 |
| 4,962,036 | 10/1990 | Cermák et al. | 435/34 |
| 4,964,310 | 10/1990 | Schneider | 73/866 |
| 5,011,662 | 4/1991 | Noormohamadi et al. | 422/68.1 |
| 5,039,617 | 8/1991 | McDonald et al. | 436/69 |
| 5,047,211 | 9/1991 | Sloane, Jr. et al. | 422/73 |
| 5,057,428 | 10/1991 | Mizutani et al. | 435/285 |
| 5,089,422 | 2/1992 | Brubaker | 435/69 |
| 5,127,278 | 7/1992 | Benz | 73/866 |
| 5,137,031 | 8/1992 | Guirguis | 128/771 |
| 5,139,031 | 8/1992 | Guirguis | 128/771 |
| 5,142,930 | 9/1992 | Bart et al. | 73/866 |
| 5,224,489 | 7/1993 | Guirguis | 128/771 |
| 5,260,872 | 11/1993 | Copeland et al. | 364/413.07 |
| 5,276,383 | 1/1994 | Leighton et al. | 435/291 |
| 5,316,730 | 5/1994 | Blake et al. | 422/73 |
| 5,339,830 | 8/1994 | Blake, III | 128/771 |
| 5,358,680 | 10/1994 | Guirguis | 422/58 |
| 5,372,945 | 12/1994 | Alchas et al. | 435/267 |

OTHER PUBLICATIONS

Nguyen et al, *P.S.E.B.M.*, vol. 92, pp. 261–269, 1992.

Transport Phenomena and Clot Dissolving Therapy: An Experimental Investigation of Diffusion–Controlled and Permeation–Enhanced Fibrinolysis—Wu, Siddqui, & Diamond. (1994) pp. 105–112.

Flow Through Clots Determines the Rate and Pattern of Fibrinolysis—Blinc, Kennedy, Bryant, Marder, & Francis. (1994) pp. 230–235.

Brubaker, D.B., "An In Vitro Bleeding Time Test", Am. Jnl. of Clinical Path., vol. 91, No. 3, Apr. 1989, pp. 422–429.

Nguyen et. al., "Thrombolysis Using Liposomal Encapsulated Streptokinase: An In Vitro Study", P.S.E.B.M. vol. 192 (1989), pp. 261–269.

*Primary Examiner*—Cecilia J. Tsang
*Assistant Examiner*—Abdel A. Mohamed
*Attorney, Agent, or Firm*—Wells, St. John, Roberts, Gregory & Matkin, P.S.

[57] ABSTRACT

A clot lysis time determining device for determining the time necessary for fluid to lyse a clot. The device comprises: a body defining a chamber; a fluid receiving inlet port to the body in fluid communication with the chamber, the inlet port permitting fluid to flow into the chamber; a fluid discharging outlet port to the body in fluid communication with the chamber, the outlet port permitting fluid to flow out from the chamber; the inlet port, chamber, and outlet port defining a communicating fluid passageway; a body opening formed in the body along the fluid passageway, the body opening permitting a portion of fluid to flow against a clot supported by clot-supporting porous membrane; and a membrane cover detachably connectable to the body and configured for holding a clot-supporting porous membrane over the body opening.

6 Claims, 14 Drawing Sheets

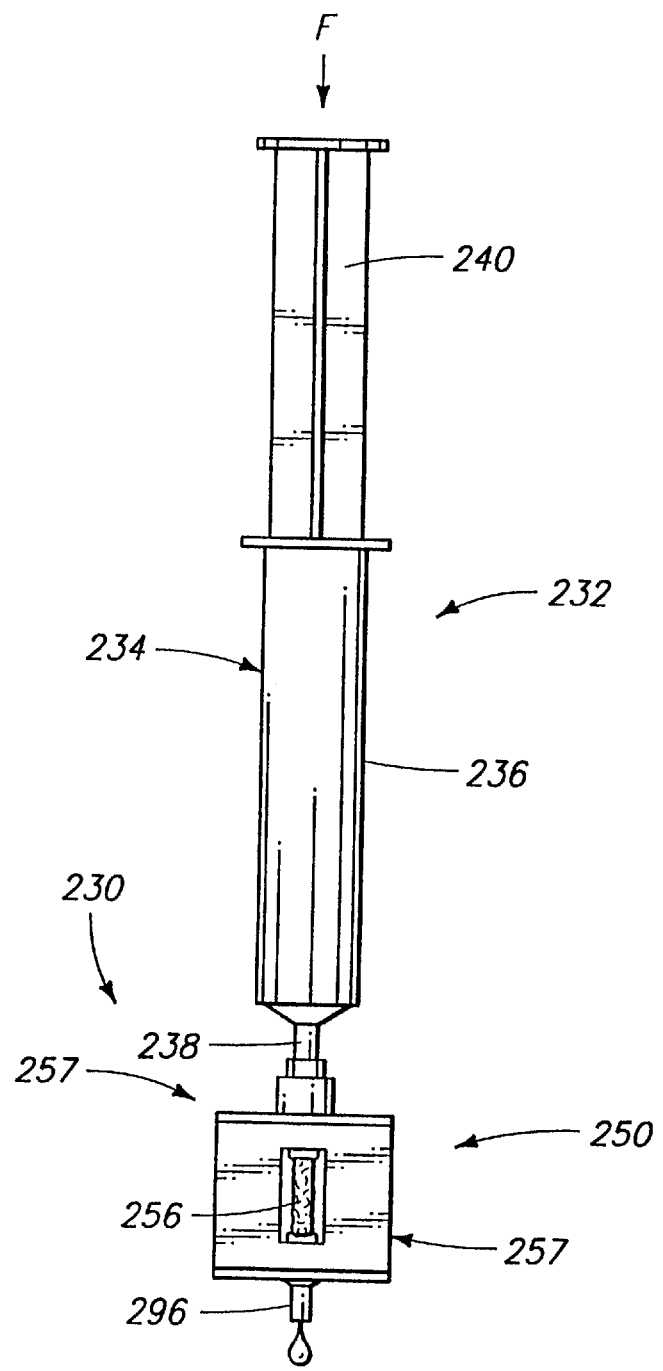

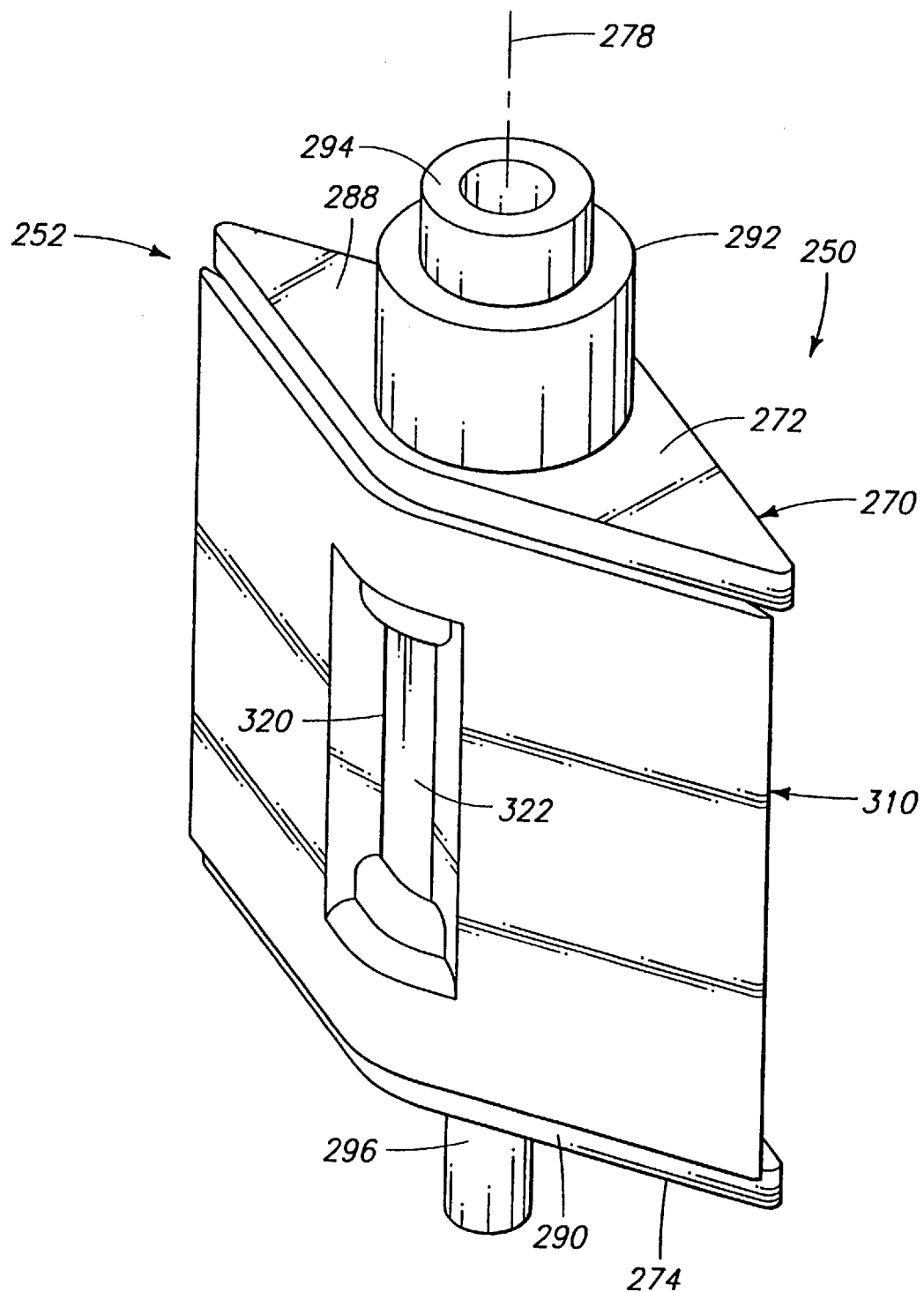

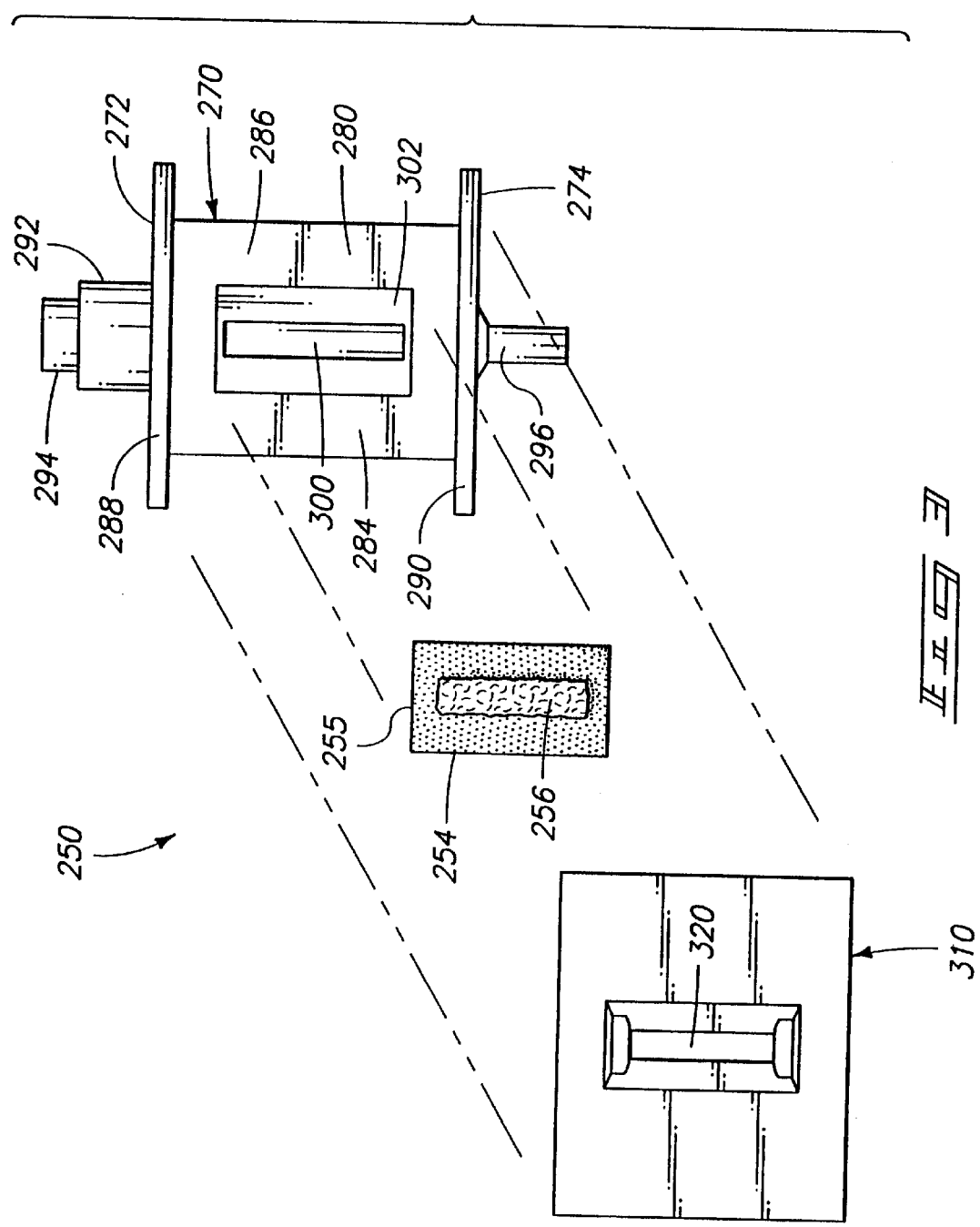

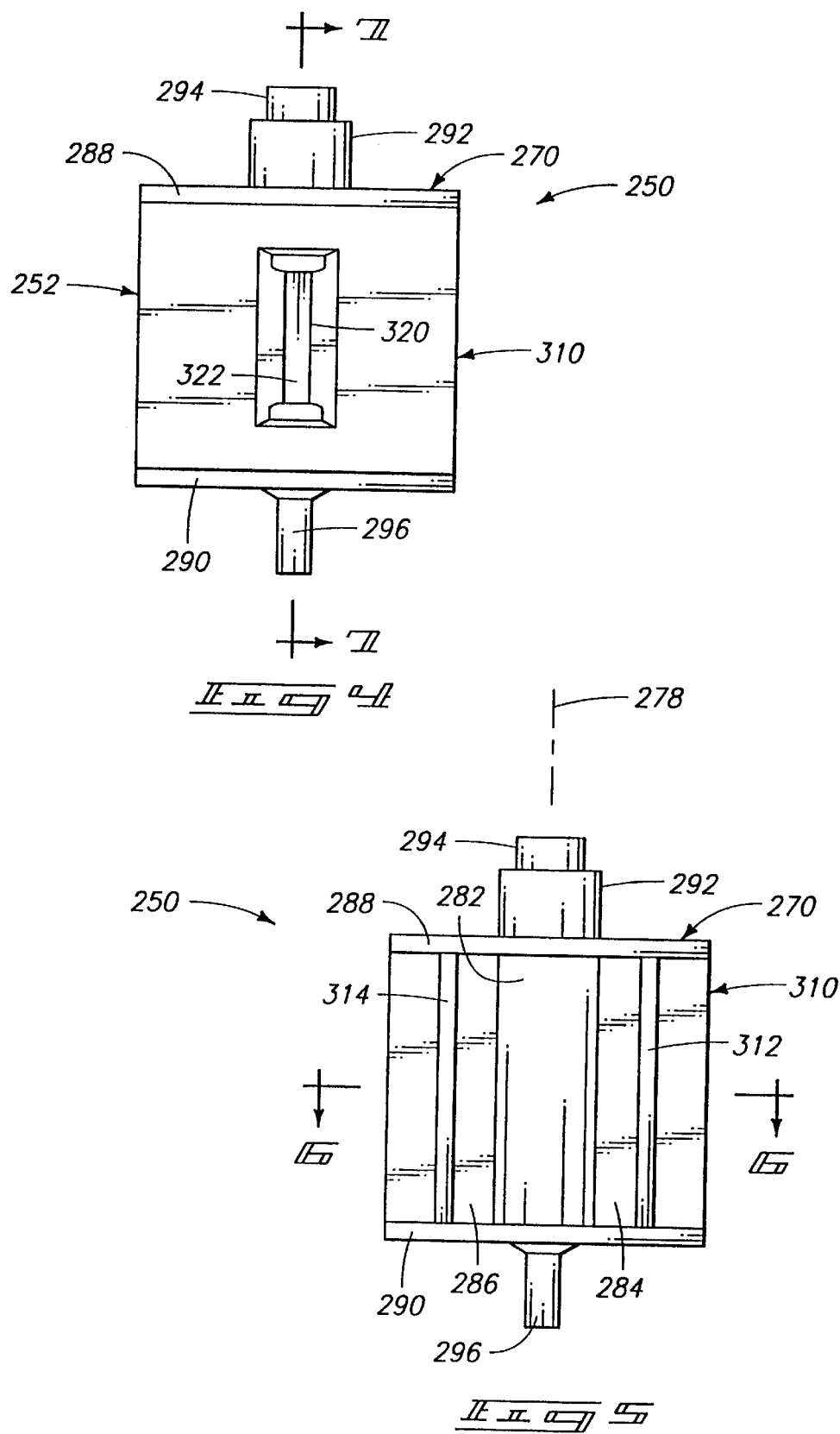

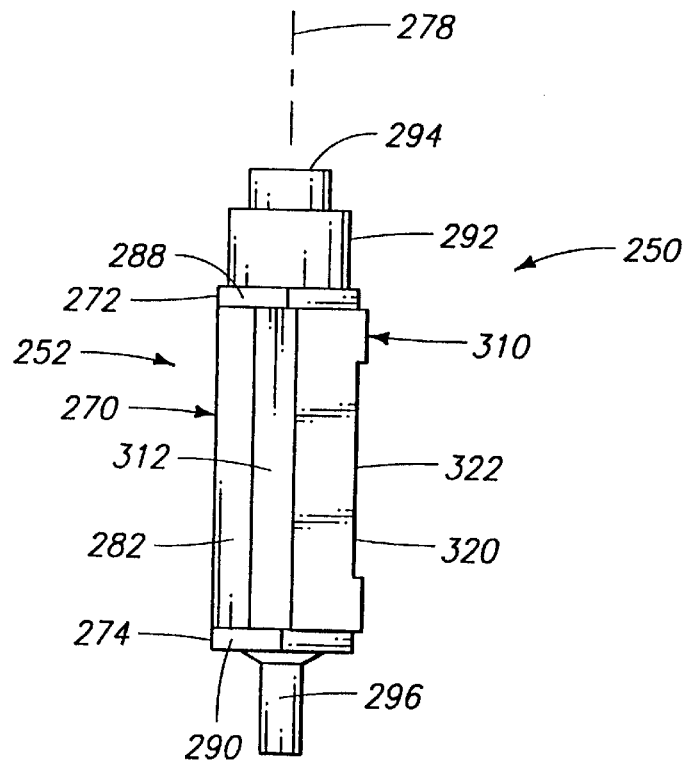
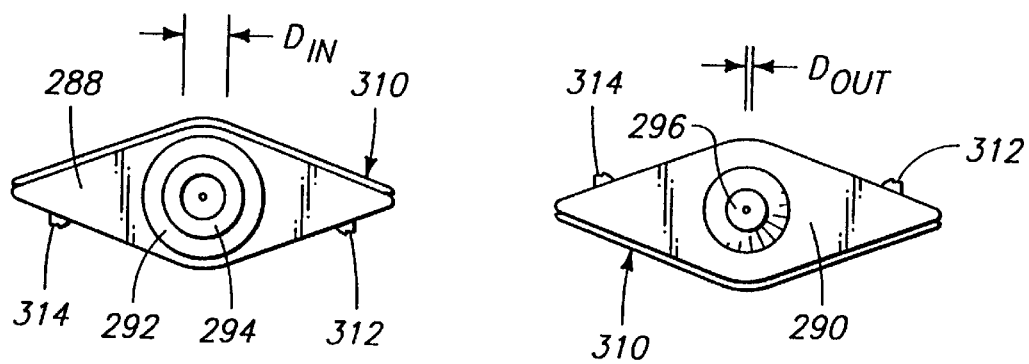

METHODS OF FORMING A PRE-CLOTTED CLOT SUPPORTER, METHODS OF STORING A PRE-CLOTTED CLOT SUPPORTER AND CLOTS ADHERED TO FLUID PERMEABLE MEMBRANES

RELATED PATENT DATA

This patent is a divisional application of U.S. patent application Ser. No. 08/431,276, entitled "Clot Lysis Time Determining Device and Method for Determining the Time Necessary for Fluid to Lyse a Clot, and Clot Supporter", filed Apr. 28, 1995, which is now U.S. Pat. No. 5,612,187, which is a continuation-in-part patent application of U.S. patent application Ser. No. 08/216,189, entitled "Device For In Vitro Bleeding Time Determination", filed Mar. 22, 1994, which is now U.S. Pat. No. 5,432,084.

TECHNICAL FIELD

This invention relates to clot lysis time determining devices for determining the time necessary for a fluid to lyse a clot.

BACKGROUND OF THE INVENTION

Clot lysis time determinations are important clinical tests. Clot lysis, or thrombolysis, occurs through fibrinolysis. In the body, fibrinolysis is carefully coordinated with coagulation so that prompt control of bleeding can occur through coagulation, and yet eventual resolution and healing can occur through fibrinolysis.

Blood clotting is a very complex series of events triggered by damage to a blood vessel. Clot formation is essential for preventing continuous bleeding. A clot is composed of platelet and fibrin, (predominately fibrin) as the clot matures. This is known as insoluble fibrin. However, sometimes clots form for other reasons and cause several problems including heart attacks, strokes, and embolisms. The clotting system is counter-acted by the fibrinolytic system naturally present in the body. This system breaks up the clot which is mostly composed of fibrin, thus the term fibrin-o-lysis. Lysis means break apart or degrade.

Fibrin formation (coagulation) and dissolution (fibrinolysis) are thought to occur simultaneously during wound clotting and healing. Studies of pathologic thrombosis support this concept of clot remodeling and indicate that the balance of the two opposing processes varies in different areas of a single large clot. Thus, there is a complex interaction between activation and inhibition of fibrinolysis.

Practitioners of medicine must be careful when altering the interaction of coagulation and fibrinolysis because pharmacological intervention can produce symptoms of bleeding and thrombosis, as well as correct symptoms of bleeding and thrombosis. For instance, disruption of the body's control of fibrinolysis can, by shifting the balance of clot formation and dissolution, lead to bleeding if there is inappropriate fibrinolytic inhibition. The bleeding caused by excess fibrinolytic stimulus can be corrected by administration of a fibrinolytic inhibitor. However, if the patient is predisposed to venous thrombosis or disseminated intravascular coagulation (DIC), clinical thrombosis could occur when the fibrinolytic inhibitor is given.

Bleeding may result either from defective inhibition, or from excessive activation of fibrinolysis. Conversely, either defective activation, or excessive inhibition of fibrinolysis can lead to thrombosis. The fact that therapy with fibrinolytic agents may dissolve a thrombus, and may also lead to bleeding, complicates clinical management. Also, the fact that antifibrinolytic therapy may stop bleeding due to excess fibrinolysis, or may lead to thrombotic complications, complicates clinical management. For instance, stimulation of fibrinolysis through therapeutic administration of plasminogen activator for treatment of thrombosis may result in uncomplicated thrombolysis, or may result in bleeding complications in susceptible patients.

Thus, the need to accurately determine the fibrinolytic capabilities of a patient's blood is critically important. Successful therapy, that is, restoration of effective hemostasis or achievement of thrombolysis without complications depends critically on selection of the appropriate treatment for the patient. Clearly, the balance between coagulation and fibrinolysis influences the occurrence and clinical course of thrombotic disease.

The fibrinolytic system is much less understood then the clotting system. The fibrinolytic system is activated through the release of tissue plasminogen activator from blood vessel endothelial cells. Tissue plasminogen activator (t-PA) activates plasminogen on the surface of clots. Fibrin degradation products (FDPs) are released from the lysed clot when it is digested. FDPs are small fragments which result from the digestion of fibrin. The FDPs, called D, X, Y, and E fragments, can be measured. These fragments, along with fibrin degradation products, fibrinogen, and plasmin, are all part of the fibrinolysis cascade and are the only elements measured. They are the end result of fibrin degradation. Low levels of FDPs, seen in the serum of patients after surgery or trauma, appear to have little effect on the coagulation systems. However, fragment degradation products seen in DIC or with fibrinolytic therapy may have an inhibitory effect on the bleeding time and coagulation screening tests. These products may also contribute to the defect in fibrin formation in these patients.

Fibrinolytic therapy with tissue plasminogen activator, urokinase, or streptokinase can cause lysis of fibrin as well as lysis of fibrinogen. Fibrin degradation products are distinguished from fibrinogen degradation products by the presence of Factor XIII cross-linkage of fibrin D domains. Commercial kits for immunologic detection of "D-D" dimers are available to detect a "segment or portion" of fibrinolysis. Currently, there are techniques available to measure static parameters of fibrinolysis, such as the end results of the fibrinolytic pathway (e.g., D-dimers), but there is nothing to measure the dynamics of fibrinolysis.

Rheology is a general term for the study of blood flow or any deformation of flow. Rheology is pertinent for coagulation processes. There are three important characteristics of blood clotting and lysis of the clot. These characteristics are: (1) the vascular integrity (e.g., structure—internal and external elastic membrane of a vessel, and function—the endothelial cells, smooth muscle cells, and fibroblasts); (2) the blood within the vessel (e.g., the cells, coagulation proteins, inhibitors, etc.); and (3) the flow of blood through the vessels and across the endothelial cells.

Among the current tests for determining the fibrinolytic capability of a fluid are tests which involve measurement of the levels present of various chemicals and proteins involved in the fibrinolytic pathway such as fibrinogen and factor XIII, or measurement of the chemicals and proteins involved in the plasmin/plasminogen cascade that induces lysis of fibrin. The chemicals and proteins involved in the fibrinolysis cascade include plasminogen, tissue plasminogen activator, serine protease plasmin, tissue plasminogen activator inhibitor, and alpha 2-antiplasmin. The total concentration of these chemicals and proteins can be measured immunologically or by chromogenic assays. The degree of fibrinolysis can be assessed indirectly by the measurement of fibrin degradation products.

Currently, screening tests for fibrinolysis are extremely limited. The thrombin clotting time will detect an abnormality in fibrinogen, but otherwise chromogenic and immunological assays of specific proteins must be performed. A diagnosis of an increased fibrinolytic state requires further assessment, often beginning with the global clot lysis time. Clot Lysis Time (CLT) measures the action of plasminogen activators and plasmin in the blood and is usually performed on clots formed from the euglobulin fraction of the plasma or whole blood. In these tests, inhibitors of activators and plasmin are removed by precipitation of plasma or whole blood at low ionic strength and low pH. After removal of the supernatant fluid, the precipitate is resuspended in an appropriate buffer and clotted with thrombin, and the time required for clot lysis is recorded. Abnormally short lysis times (less then 2 hours) reflect acute episodes of excessive fibrinolysis that accompany a variety of acquired disorders or that result from the administration of plasminogen activators such as streptokinase. CLT is currently not a useful screening test due to the time necessary to obtain results.

A problem concerning the handling of blood, and blood-derived products, is health safety. Blood samples may carry sexually transmitted infectious agents such as HIV 1 and 2, Hepatitis B, syphilis, etc. which could infect the clinician if proper safeguards are not in place.

BRIEF DESCRIPTION OF THE DRAWINGS

One or more preferred forms of the invention are described herein with reference to the following drawings.

FIG. 1 shows a clot lysis time determination system comprising a clot lysis time determining device attached to a pressure inducing syringe.

FIG. 2 is an isometric view of the clot lysis time determining device.

FIG. 3 is an exploded front view of the of the clot lysis time determining device showing a body, a clot supported by a clot-supporting porous membrane, and a membrane cover.

FIG. 4 is a front view of the clot lysis time determining device.

FIG. 5 is a back view of the clot lysis time determining device.

FIG. 8 is a side view of the clot lysis time determining device.

FIG. 9 is a top view of the clot lysis time determining device.

FIG. 10 is a bottom view of the clot lysis time determining device.

DETAILED DESCRIPTION OF THE PREFERRED EMBODIMENTS

Figure 6:
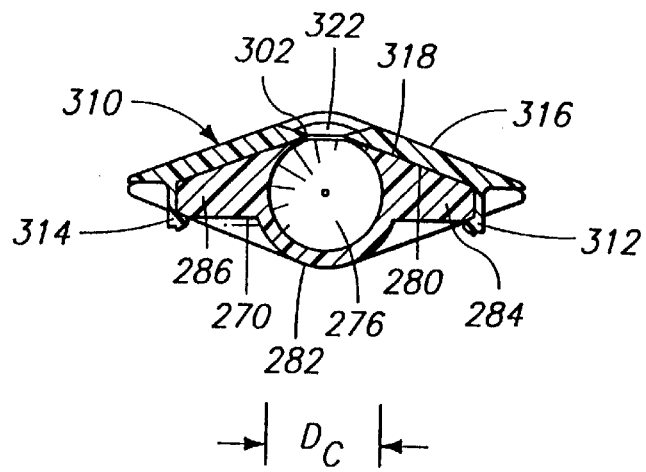
FIG. 6 is a cross-sectional view taken along line 6—6 in FIG. 5.

This disclosure of the invention is submitted in furtherance of the constitutional purposes of the U.S. Patent Laws "to promote the progress of science and useful arts" (Article 1, Section 8).

This invention is a clot lysis time determining device for determining the time necessary for a fluid to lyse a clot. The device comprises: a body defining a chamber; a fluid receiving inlet port to the body in fluid communication with the chamber, the inlet port permitting fluid to flow into the chamber; a fluid discharging outlet port to the body in fluid communication with the chamber, the outlet port permitting fluid to flow out from the chamber; the inlet port, chamber, and outlet port defining a communicating fluid passageway; a body opening formed in the body along the fluid passageway, the body opening permitting a portion of fluid to flow against a clot supported by clot-supporting porous membrane; and a membrane cover detachably connectable to the body and configured for holding a clot-supporting porous membrane over the body opening.

The time necessary for a fluid to lyse a clot provides valuable information about the fluid's clot lysing ability. The device can be used with blood, blood components, or other fluids to determine if the fluids contain the appropriate mix of factors to lyse clots within a reasonable period of time. The reasonable period of time can be established by using standards.

U.S. Pat. No. 5,089,422 describes an apparatus and method for in vitro bleeding time determination. That patent is incorporated herein by reference. This invention provides an improved, mass producible device that can be used in the apparatus described in this patent.

System

FIG. 1 shows clot lysis time determination system 230 according to this invention. System 230 has a fluid pressurizing mechanism 232 in the form of a standard syringe 234. Syringe 234 includes an elongated tube 236 for holding a supply of fluid, a discharging end 238, and a plunger 240 for displacing fluid from the tube 236 out through discharging end 238 under a force F. Syringe 234 is preferably formed of plastic, although glass and other materials can be used. Force F can be applied manually or via weights, but is preferably generated by an automatic syringe plunger depression mechanism (not shown).

Clot lysis time determination system 230 also has a clot lysis time determining device 250 that is detachably connected to discharging end 238 of pressure syringe 234. Clot lysis time determining device 250 enables the time necessary for fluid to lyse a clot to be determined. The time necessary for fluid to lyse a clot is determined by monitoring the time necessary for preformed clot 256 to be lysed.

Device 250 comprises clot holder 252. Clot holder 252 is configured to position and hold clot 256 over body opening 300 in device 250 (FIG. 3). Clot holder 252 positions and holds clot 256 by positioning and holding pre-clotted clot supporter 255 (FIG. 3) which comprises a clot-supporting porous membrane 254 and a clot 256. When clot holder 252 holds a clot 256, the clot holder and clot together comprise clot-containing clot holder 257.

As fluid discharged from the syringe is passed under force through device 250, a portion of the fluid flows though opening 300 and against clot 256 supported by clot-supporting porous membrane 254, which in turn is held by clot holder 252.

To measure clot lysis time using system 230, fluid is displaced through clot lysis time determining device 250 under force F from syringe 234. Fluid flows against the clot 256 and through outlet port 296. Eventually, clot 256 breaks apart allowing fluid to flow through porous membrane 254 which covers opening 300 (FIG. 3). The clot lysis time can be determined in several ways, including monitoring the rate of fluid flow through opening 300, monitoring the rate of fluid flow through outlet port 296, monitoring the rate at which the plunger 240 falls—if force F is kept constant, or monitoring the pressure generated by plunger 240—if the plunger is depressed at a constant rate.

Clot Lysis Time Determining Device

FIGS. 2–10 illustrate clot lysis determining device 250 in more detail. Device 250 includes a body 270 and a detachable membrane cover 310 which detachably connects to body 270 to hold clot-supporting porous membrane 254 in place against the body. In this manner, body 270 and membrane cover 310 form clot holder 252. Also, the combination of clot holder 252 with pre-clotted clot8 supporter 255 forms clot-containing clot holder 257. Pre-clotted clot-supporter 255 comprises a clot-supporting porous membrane 254 and a clot 256. Clot holder 252 is configured to hold the clot-supporting porous membrane 254 of pre-clotted clot-supporter 255 over body opening 300. Adhesive may also be used to assist in holding membrane 254 in its appropriate location. Additionally, the entire clot-containing clot holder 257 (i.e., body 270, pre-clotted clot-supporter 255, and membrane cover 310) can be bonded together to form a fluid tight seal relative to one another, for example, with triethylene chloride or by sonar welding or by other means. Body 270 and cover 310 are preferably formed of plastic, and more particularly, of polycarbonate, which does not promote blood clotting.

Body 270 is described in more detail with reference to FIGS. 2–15. Body 270 has a first, proximal upper end 272 and a second, distal lower end 274. Body 270 is hollow and thereby defines a cylindrical-shaped body cavity or chamber 276 (FIG. 6) which extends vertically along longitudinal axis 278 between the upper and lower ends 272, 274. In a preferred embodiment chamber 276 is elongated. Also, in a preferred embodiment chamber 276 is constructed such that a fluid can be pressurized within chamber 276.

Body 270 has a V-shaped front side wall 280 (FIGS. 3, 6, and 11) adjacent to chamber 276, and a cylindrical-shaped back side wall 282 (FIGS. 6 and 12) also adjacent to chamber 276. Front wall 280 extends outwardly from axis 278 to form opposing flanges 284 and 286 which are used to secure membrane cover 310 to the body. Body 270 also has a top platform 288 at the upper end 272 and bottom platform 290 at the lower end 274. The top and bottom platforms 288, 290 are diamond-shaped parallelograms (FIGS. 2, 14, and 15) which have opposing tips 289 and 291, respectively, that project beyond body flanges 284 and 286.

Figure 7:
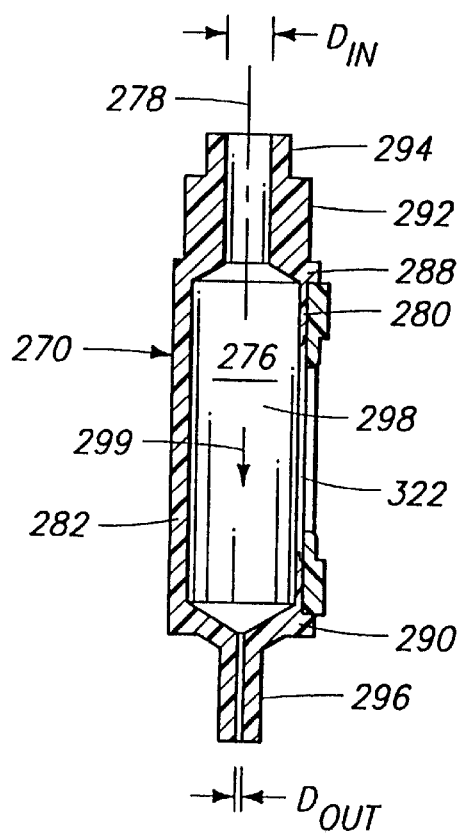
FIG. 7 is a cross-sectional view taken along line 7—7 in FIG. 4.
Figure 11:
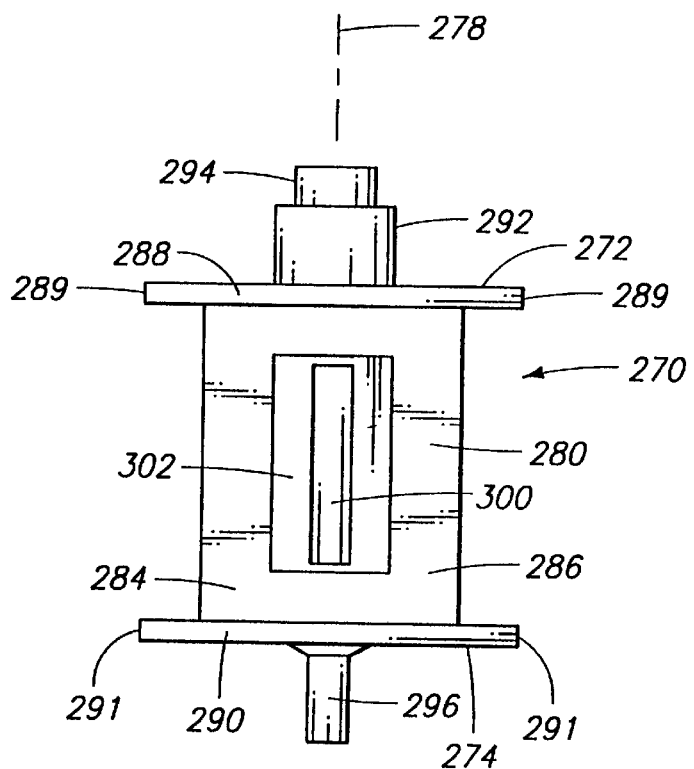
FIG. 11 is a front view of the FIG. 3 body of the clot lysis time determining device.
Figure 12:
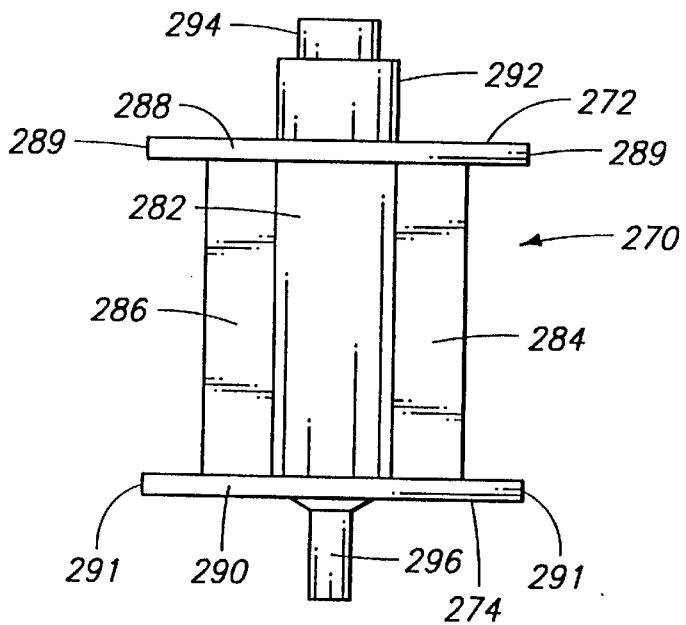
FIG. 12 is a back view of the body.
Figure 13:
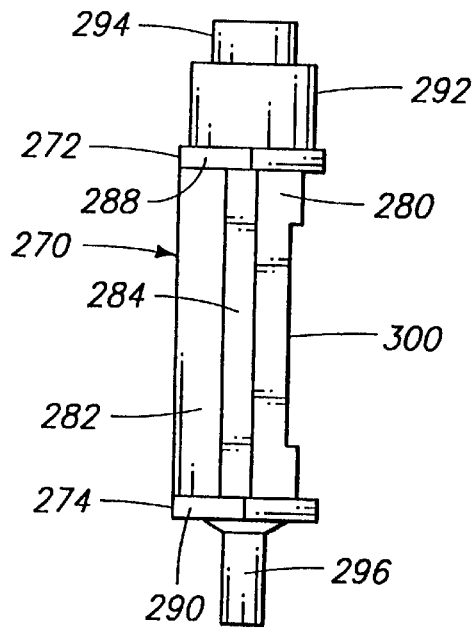
FIG. 13 is a side view of the body.
Figures 14, 15:
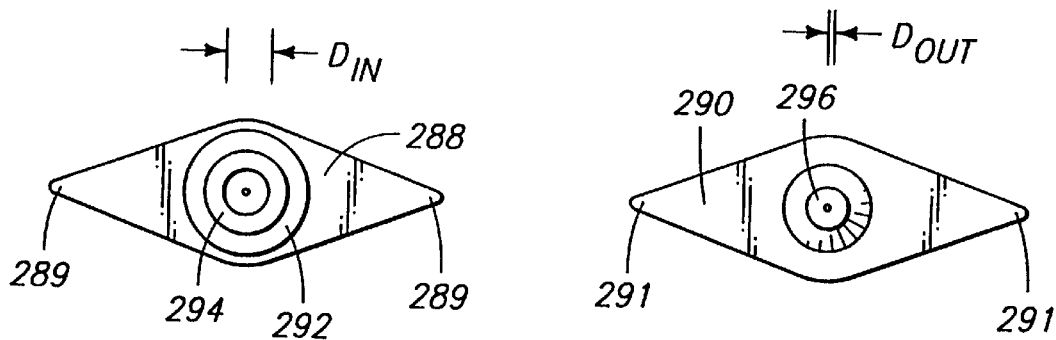
FIG. 14 is a top view of the body.
FIG. 15 is a bottom view of the body.
Figure 16:
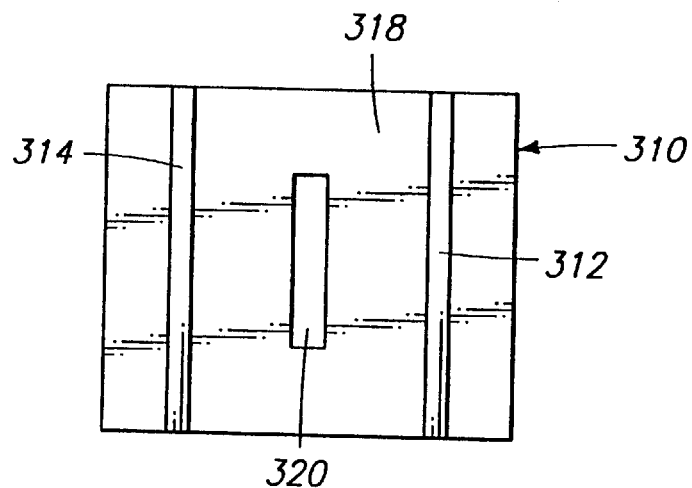
FIG. 16 is a front view of the FIG. 3 membrane cover of the clot lysis time determining device.
Figure 17:
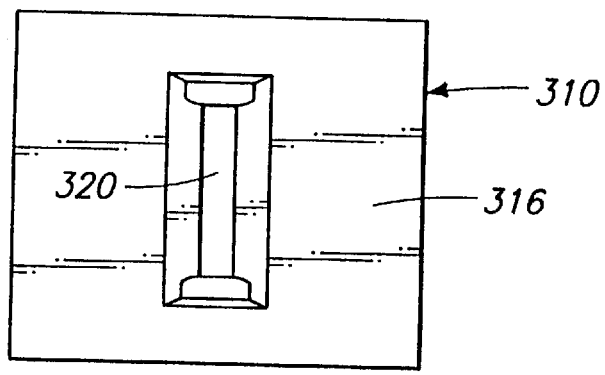
FIG. 17 is a back view of the membrane cover.
Figure 18:
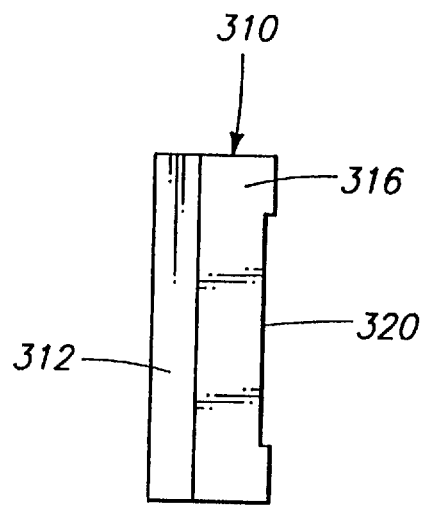
FIG. 18 is a side view of the membrane cover.
Figure 19:
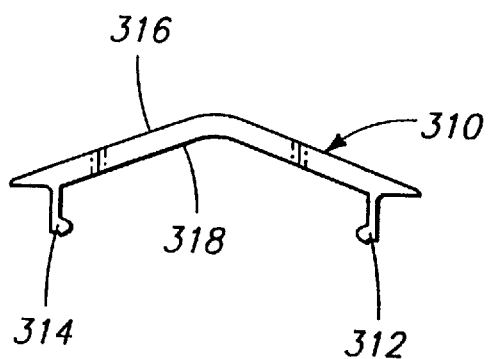
FIG. 19 is a top view of the membrane cover.

Clot lysis time determining device 250 has a fluid receiving inlet port 292 provided at the body upper end 272 adjacent to top platform 288. Inlet port 292 is preferably cylindrically shaped and extends along longitudinal axis 278. Inlet port 292 defines a proximal aperture in fluid communication with chamber 276 of body 270 to permit fluid to flow into the chamber. As shown in FIGS. 7 and 9, inlet port 292 has an inner diameter $D_{IN}$ which defines a first cross-sectional area. Inlet port 292 also forms in part a detachable coupling collar 294 that is sized to sealingly attach to the discharging end 238 of syringe 234 (FIG. 1). Coupling collar 294 is preferably a friction mount which slides onto syringe end 238, but can also include threaded or other coupling arrangements.

A fluid discharging outlet port 296 is provided at the body lower end 274 adjacent to bottom platform 290. Outlet port 296 is preferably cylindrical shaped and extends along longitudinal axis 278. Outlet port 296 defines a distal aperture in fluid communication with chamber 276 of body 270 to permit fluid to flow out from the chamber. As shown in FIGS. 7 and 10, outlet port 296 has an inner diameter $D_{OUT}$ of approximately 0.1–0.2 centimeter.

It is noted that in a preferred embodiment outlet port 296 has a second cross-sectional area that is less than the first cross-sectional area of inlet port 292. Additionally, chamber 276 has a diameter DC (FIG. 6) which is at least equal to, and can be slightly larger than, the diameter $D_{IN}$ of inlet port. Alternatively, chamber 276 can taper from inlet port 292 to outlet port 296 to form a conical cavity, or as another example, taper from a location just below the body opening toward the outlet port.

Inlet port 292, chamber 276, and outlet port 296 define a communicating fluid passageway 298 (FIG. 7) that extends approximately vertically along longitudinal axis 278 between the upper and lower ends. Fluid passageway 298 is preferably elongated between the upper and lower ends. Fluid flows downward through vertical fluid passageway 298 from inlet port 292, through body cavity 276, to outlet port 296 as indicated by arrow 299.

A body opening 300 is formed in front side wall 280 of body 270. Body opening 300 is a rectangular aperture, elongated relative to axis 278. Body opening 300 opens into fluid passageway 298. Body opening 300 is preferably 0.2–0.3 centimeters wide and about 0.8 centimeters long. Thus, body opening 300 preferably has a larger cross-sectional area than that of outlet port 296. A recessed mounting area 302 is indented in front side wall 280 (FIGS. 3, 6, and 11) surrounding opening 300 to accommodate clot-supporting membrane 254 (FIG. 3). Porous membrane 254 extends across opening 300, and can be secured at its outer edges to recess mounting area 302 via an appropriate adhesive.

A preformed clot 256 (FIG. 3) is adhered to membrane 254, and supported on clot supporting porous membrane 254 such that when the membrane is mounted over opening 300, the clot is provided over the body opening (FIGS. 1 and 3). Clot holder 252, which comprises membrane cover 310 and body 270, is configured to releasibly position clot-supporting porous membrane 254 over body opening 300. By releasibly positioning clot-supporting membrane 254 over body opening 300, clot holder 252 releasibly positions a clot 256 which is supported by membrane 254 over body opening 300. During operation, fluid passes under pressure along fluid passageway 298. Body opening 300 (FIG. 11), formed in the body along the fluid passageway, permits a portion of the fluid to flow against clot 256 supported by clot-supporting porous membrane 254.

Membrane cover 310 of clot lysis time determining device 250 is described in more detail with reference to FIGS. 2–10 and 16–19. Membrane cover 310 is designed to attach to body 270 and thereby hold membrane 254 against body 270 and over body opening 300. This arrangement enables membrane cover 310 to firmly hold a clot 256, supported by clot-supporting membrane 254, over body opening 300. In the preferred embodiment, cover 310 has two deflectable clips 312 and 314 which releasibly snap onto respective flanges 284 and 286 of body 270 (FIGS. 5 and 6). Thus, membrane cover 310 is detachably connectable to the body and configured for holding clot-supporting porous membrane 254 over body opening 300.

Detachable membrane cover 310 has a V-shape that conforms to the contour of front side wall 280 of body 270. Cover 310 has an outside surface 316 and an inside surface 318. When the cover is attached to the body, inside surface 318 abuts front side wall 280. Membrane 254 is held in recessed mounting area 302 by being sandwiched between inside surface 318 of cover 310 and front side wall 280 of body 270.

A cover opening 320 is formed in the center of membrane cover 310. Cover opening 320 is a rectangular aperture elongated relative to longitudinal axis 278 and is approximately the size of body opening 300 (i.e., 0.2–0.3×0.8 centimeters), although it can, of course, be other sizes and shapes. When membrane cover 310 is attached to body 270, cover opening 320 is aligned with body opening 300 to form a single window 322 to chamber 276. The clot-supporting membrane 254, when mounted in clot holder 252, is held suspended within window 322 in contact with the fluid passageway 298.

To prepare the clot lysis time determining device 250 for use in tests to determine the clot lysing ability of fluids, membrane cover 310 is first detached from body 270. A pre-clotted clot-supporter 255 is laid within recessed mounting area 302 over body opening 300. Membrane cover 310 is then reattached to body 270 atop membrane 254 to hold the membrane against the body. The entire assembly is then bonded with triethylene chloride or sonar welding. The bonding has no effect on the proteins in and on the membrane. The clot lysis time determining device 250 is then ready for connection to a syringe or other fluid pressurizing mechanism to begin tests for determining the time necessary for fluid to lyse a clot.

Figure 20:
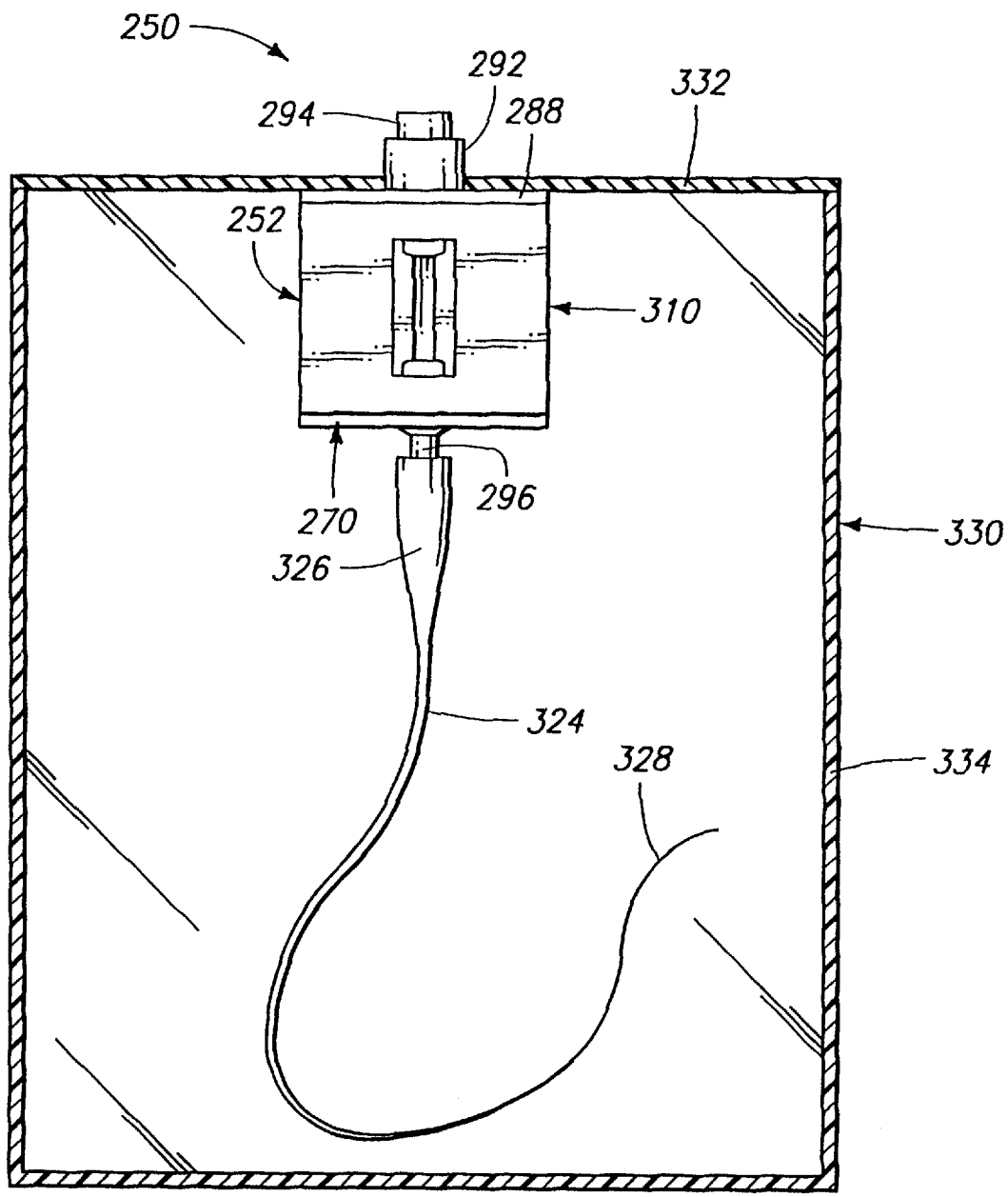
FIG. 20 is a partial cross-sectional view illustrating the clot lysis time determining device housed within a fluid collection reservoir.

FIG. 20 shows an elongated constricting tube 324 coupled to outlet port 296. Tube 324 defines a continuously constricting fluid channel that is in fluid communication with outlet port 296 and fluid passageway 298 so that fluid flowing through body 270 can exit through lower end port 296 and tube 324. More particularly, tube 324 has a cross-sectional area that decreases from a proximal end 326 connected to outlet port 296 to a distal end 328. The inner diameter at distal end 328 is preferably 100–500 microns. Tube 324 is preferably twelve inches in length. Tube 324 thereby simulates a constricted blood vessel distal to the cut site. The constricting tube slows fluid flow distal to body 270.

FIG. 20 also shows clot lysis time determining device 250 housed within a fluid collection reservoir 330. Reservoir 330 has a lid 332 that is attached to top platform 288 of body 270 and/or inlet port 292. Reservoir 330 has a container 334 that encompasses body 270 and outlet port 296. Lid 332 is connected to container 334 to form an entirely enclosed reservoir. When assembled, reservoir 330 collects fluid that flows through (a) window 322 formed by body opening 300 and cover opening 320 and (b) outlet port 296 and tube 324. Reservoir 330 is preferably formed of clear plastic so that the technician performing the clot lysis time tests can view the apparatus during the tests. Other clear materials, such as glass, can also be used.

This invention enables an inexpensive testing device for determining the time necessary for fluid to lyse a clot. Once the device is used for one or more tests of a patient's blood, blood components, or other body fluids, the device can simply be detached from the syringe or other. fluid pressurizing mechanism and discarded. The disposable device is safe and lowers the health risks associated with handling potentially infectious blood and blood derived products. The fluid discharged from the clot lysis time determining device is completely captured within the enclosed reservoir. There is no human contact with potentially tainted body fluids, making the experimentation and disposal processes efficient and safe.

Pre-clotted Clot-Supporter

Pre-clotted clot-supporter 255 is described in more detail with reference to FIG. 3. Pre-clotted clot-supporter 255 comprises clot supporting porous membrane 254 and clot 256 adhered to the membrane. In the preferred embodiment, membrane 254 comprises a nylon mesh. Preferably the membrane comprises a mesh with a mesh opening from about 30 to about 100 micrometers. Most preferably the membrane comprises a mesh with a mesh opening greater than or equal to about 40 micrometers, which is larger than most red blood cells. The pre-clotted clot-supporter 255 is preferably stored in a buffer containing hydroxy succinimide and benzimidazopyridazinone (BDD) (the buffer also contains 0.3M NaCl, 5 mM $CaCl_2$, 0.05M Tris-HCl, pH 7.4).

Pre-clotted clot-supporter 255 is made in the following manner. A mesh, preferably a nylon mesh with a mesh opening of 60 micrometers, is first layered with 0.1 molar hydroxy succinimide (a crosslinking material). Cryoprecipitate, prepared with 0.2 millimoles per liter of BDD is pre-incubated with glu-plasminogen at 37 degrees Celsius for 20 minutes at a final concentration of 2.5 micromoles. The cryoprecipitate is then added to overlay the mesh. Cryoprecipitate is the cold insoluble fraction of plasma which is prepared in blood centers throughout the world. This is used because fibrinogen and factor XIII are concentrated in this product. All donors of blood are screened for viruses such as Hepatitis and HIV, so the blood derivatives used for making the pre-clotted clot-supporter should be free of these viruses.

Next, 1–3 units per milliliter of thrombin (in a buffer containing 0.3M NaCl, 5 mM $CaCl_2$, 0.05M Tris-HCl, pH 7.4) is added to initiate a clot interwoven with the membrane. After thrombin is added to the buffer, the clot is incubated at 37° Celsius for 30–60 minutes. The membrane is stored at 4° Celsius, preferably in a buffer containing 0.3M NaCl, 5 mM $CaCl_2$, 0.05M Tris-HCl, pH 7.4, with 0.2 millimoles per liter of BDD to minimize clot retraction.

When insoluble fibrin becomes dried it is very brittle and cracks. This is also true when too much thrombin is added to fibrinogen. To minimize the brittleness of the preformed clot a very small amount of thrombin is preferably used to initiate clot formation.

The 0.3M NaCl, 5 mM $CaCl_2$, 0.05M Tris-HCl, pH 7.4 buffer is prepared by first making a 0.05M Tris-HCl solution at a pH of 7.4, and then adding $CaCl_2$ to a concentration of 5 millimolar and NaCl to a concentration of 0.3 molar.

The clot supporter can preferably comprise proteins which can be part of the clot or adhered to the membrane.

An example would be proteins which affect fibrinolysis, such as plasminogen activator (an inhibitor) or tissue plasminogen activator (a promoter). The clot could also be derived from and constitute living biological material, such as endothelial cells.

Method of Operation

Figure 21:
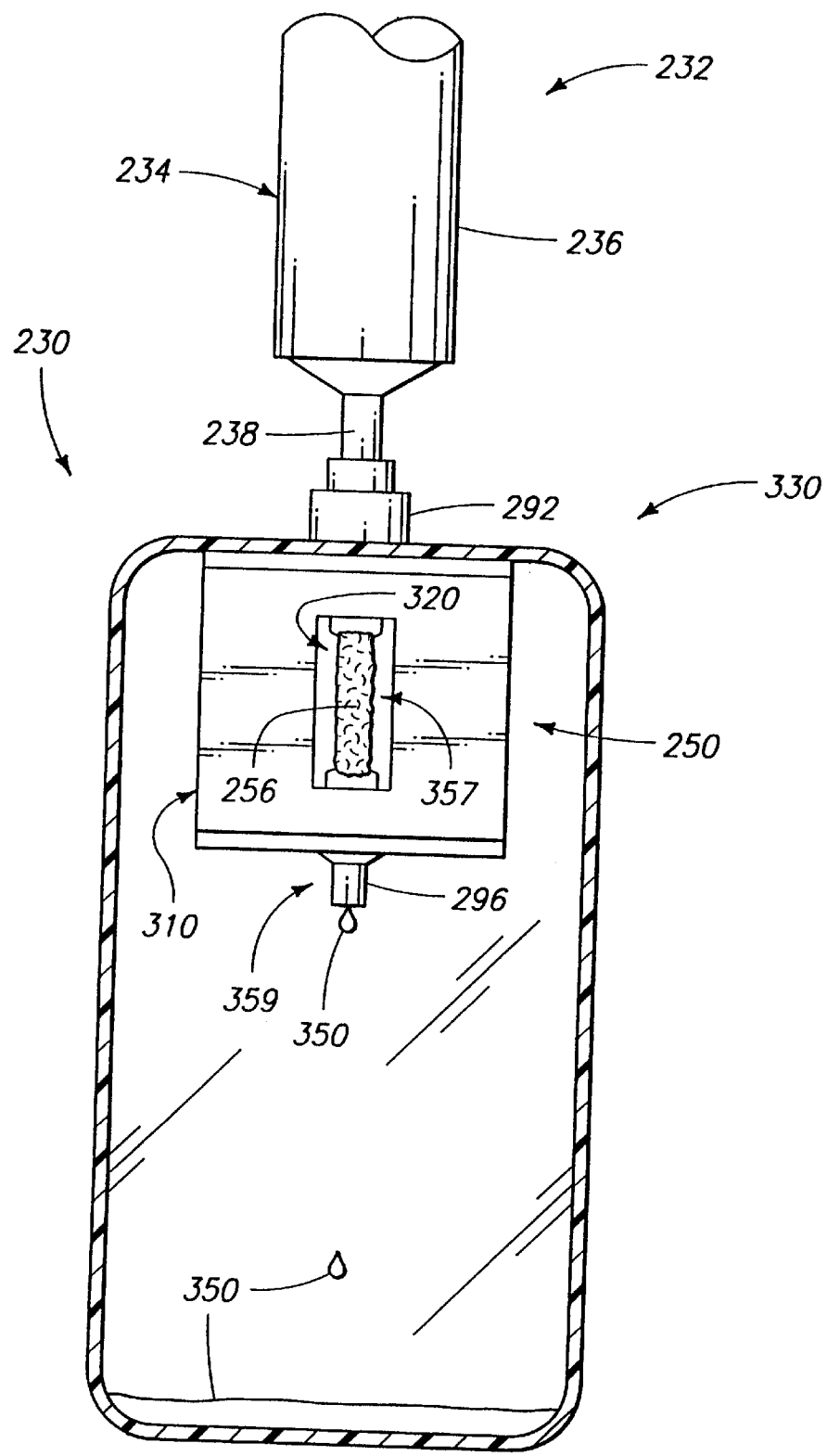
FIG. 21 is a partial cross-sectional view of the lysis time determining system in operation showing the system in its pre-clot-lysis mode.
Figure 22:
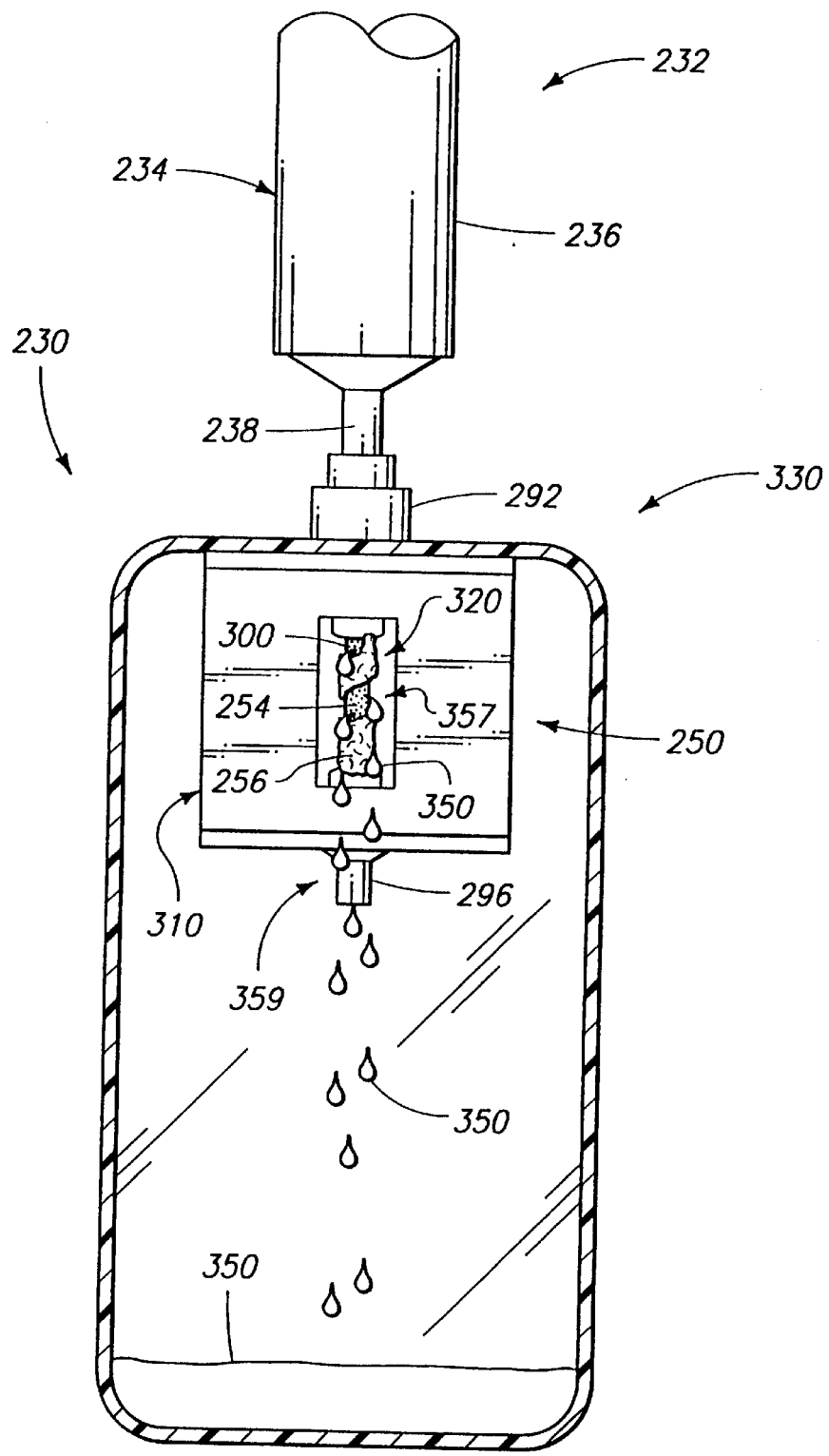
FIG. 22 is a partial cross-sectional view of the clot lysis time determining system in operation showing the system in its post-clot-lysis mode.

FIGS. 21 and 22 illustrate a preferred method of operation of clot lysis time determining system 230. FIG. 21 shows the system in a pre-clot-lysis mode, (i.e., in a mode in which a clot 256 is still fully intact), and FIG. 22 shows the system in a post-clot-lysis mode (i.e., in a mode in which clot 256 is no longer fully intact). In practice the system is initially in the pre-lysis mode, and a fluid 350 that is to be tested is flowed through the system until either the post-lysis mode is reached, or until so much time has elapsed that it is clear that the fluid is deficient in its clot lysing ability.

Referring to FIG. 21, the system consists of syringe 234 and clot lysis time determining device 250. FIG. 21 shows system 230 used in conjunction with a reservoir 330. Fluid 350 enters device 250 at inlet port 292 and exits at outlet port 296 into reservoir 330. In the pre-clot-lysis mode illustrated in FIG. 21 preformed clot 256 is intact, and is blocking body opening 300 (body opening 300 is not shown in FIG. 21 because it is obstructed by clot 256). Clot 256 is visible through cover opening 320 in membrane cover 310.

In the pre-clot-lysis mode the fluid that flows into body opening 300 flows against clot 256. Clot 256 impedes a path of flow shown generally at 357. Thus, the fluid 350 is flowing through a passageway which contains at least two paths of flow, with at least one of the paths being impeded by a clot, shown generally at 357, and least one of the other paths being unimpeded by a clot, shown generally at 359. As shown in FIG. 21, fluid 350 exits device 250 predominantly via path 359 in the pre-clot-lysis mode.

An advantage of this system, verses a static system in which fluid is not flowing when it is tested, is that the fluid 350 that is being tested is continuously flowing against clot 256, so that the clot is continuously exposed to fresh lysing components that are in the fluid which is being tested. This is helps to make this system a relatively fast test.

In FIG. 21, the path of flow impeded by a clot is shown generally at 357. This path of flow can be more clearly seen in FIG. 22 which illustrates the post-clot-lysis mode of the system. In FIG. 22, clot 256 is shown to be broken and fluid 350 is shown exiting around and through the remnants of clot 256. The fluid that exits around and through the remnants of clot 256 is flowing through opening 300 (which is beneath porous membrane 254), through porous membrane 254, and exiting device 250 through cover opening 320 in membrane cover 310. In other words, in the post-clot-lysis mode shown in FIG. 22, fluid 350 exits device 250 through the path of flow 357 that was previously impeded by clot 256 in the pre-clot-lysis mode shown in FIG. 21.

In the preferred embodiment shown in FIG. 22, the path unimpeded by a clot in the pre-clot-lysis mode, path 359, has a narrower cross-sectional area then the path impeded by a clot in the pre-clot-lysis mode, path 357.

The time necessary for a fluid to lyse a clot is determined as the time necessary for the system to go from the pre-clot-lysis mode to the post-clot-lysis mode. This time is determined by monitoring a flow condition of fluid 350 as it is flowed through system 230. The flow condition monitored can be the amount of fluid exiting path 357, the amount of fluid exiting path 359, the pressure of fluid in system 230, or the flow rate of fluid through system 230. Such might be determined by measuring either of positive or negative fluid pressure, distance of syringe plunger travel, optical monitoring, electrical and/or digital technology, laser, radar, or others, or some combination of techniques.

Figure 23:
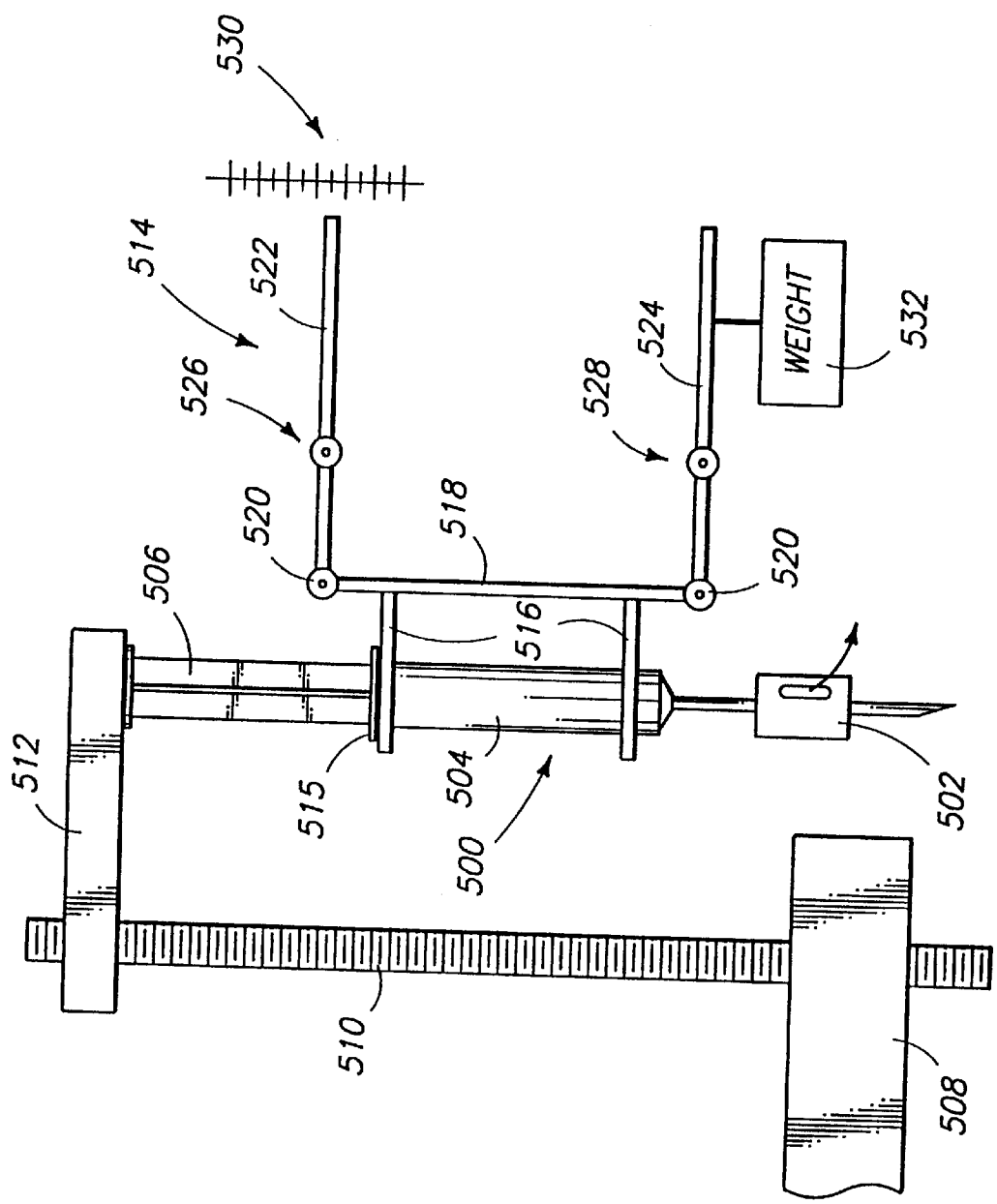
FIG. 23 is a diagrammatic representation of a system for measuring flow rate of fluid through the device.

One example preferred technique for monitoring flow through the device is illustrated diagrammatically in FIG. 23. A syringe 500 connects with a device of the invention schematically indicated with reference numeral 502. Syringe 500 comprises a barrel portion 504, a flange 515 and a plunger portion 506. A plunger driving device includes a stepper motor 508, a lead drive screw 510 and a horizontal bar extending from lead screw to drive syringe plunger 506 downwardly to cause fluid to exit the device 502.

An apparatus 514, in cooperation with lead screw 510, facilitates maintaining constant pressure of flowing fluid within device 502. Apparatus 514 includes a pair of projecting supports 516 which are received slidably about syringe body 504. The upper support 516 engages and bears against syringe flange 515. Supports 516 extend laterally outward from a vertically oriented bar 518. Such is connected at its upper and lower ends to a pair of hinges 520. A pair of bars 522 and 524 extend laterally from the respective hinges 520, and are pivotal relative to a pair of fixed pivot points 526 and 528, respectively. The outer end of bar 522 is indexed relative to a scale 530. A weight 532 connects to lower bar 524, and is selectively positionable relative thereto from its outer right end to the illustrated pivot point. Such has the effect of a lever, thereby applying greater or lesser upward force of upper support 516 against flange 515 and thus the pressure applied to fluid within syringe 500.

In operation, the device would be established as shown with the weight positioned as desired to provide a predetermined pressure of the fluid within syringe 500. Were lead screw 510 to remain stationary, the resultant action would be upward movement of supports 516 the result of fluid being able to exit the system through the end of the syringe beneath device 502, or laterally through device 502. Accordingly, the pointer end of bar 522 would move or point downwardly relative to scale 30. Constant pressure is maintained, however, by stepper motor 508 driving lead screw 510 such that the position of the outer end of arm 522 remains constant relative to its starting position on scale 530. The incremental movements of lead screw 510 by stepper motor 508 are monitored, and correspondingly flow rate through the device is determined. As the clot lyses, the flow rate increases such that lysis can be determined by a significant increase in flow rate.

In compliance with the statute, the invention has been described in language necessarily limited in its ability to properly convey the conceptual nature of the invention. Because of this inherent limitation of language, it must be understood that the invention is not necessarily limited to the specific features described, since the means herein disclosed comprise merely preferred forms of putting the invention into effect. The invention is, therefore, claimed in any of its forms or modifications within the proper scope of the appended claims appropriately interpreted in accordance with the doctrine of equivalents.

I claim:

1. A method of forming and storing a clot comprising:
    adding thrombin to a cryoprecipitate to initiate clot formation from the cryoprecipitate and form a clot on a clot supporting porous membrane;
    after initiating clot formation, incubating the clot at 37° C. for 30–60 minutes: and
    after the incubating and while the clot is on the clot supporting porous membrane, storing the clot in a solution containing hydroxy succinimide and benzimidazopyridazinone.

2. The method of claim 1 wherein the membrane comprises a nylon mesh.

3. The method of claim 1 further comprising a membrane adhered protein which affects fibrinolysis.

4. The method of claim 1 wherein the membrane comprises a mesh with a mesh opening from about 30 to about 100 micrometers.

5. The method of claim 1 wherein the membrane comprises a mesh with a mesh opening of greater than or equal to about 40 micrometers.

6. A method of forming and storing a clot comprising:

adding thrombin to a cryoprecipitate to form a clot from the cryoprecipitate the clot being formed on a clot supporting membrane; and while the clot is on the clot supporting membrane, storing the clot in a solution containing benzimidazopyridazinone.

* * * * *

UNITED STATES PATENT AND TRADEMARK OFFICE
CERTIFICATE OF CORRECTION

PATENT NO. : 5,864,017
DATED : January 26, 1999
INVENTOR(S) : Daniel B. Brubaker It is certified that error appears in the above-identified patent and that said Letters Patent is hereby corrected as shown below:

Col. 5, l. 35:   Replace "clot8 supporter" with --clot-supporter--.

Col. 6, l. 28:   Replace "DC" with --$D_C$--.

Col. 11, l. 8:   Replace "claim 1" with --claim 4--.

Signed and Sealed this

Twenty-seventh Day of July, 1999

Attest:

Q. TODD DICKINSON

*Attesting Officer*      *Acting Commissioner of Patents and Trademarks*